United States Patent
Abjanic et al.

(10) Patent No.: US 7,512,711 B1
(45) Date of Patent: Mar. 31, 2009

(54) SCALABLE NETWORK APPARATUS FOR CONTENT BASED SWITCHING OR VALIDATION ACCELERATION

(76) Inventors: John B. Abjanic, 11423 Almazon St., San Diego, CA (US) 92129; David A. Marlatt, 2136 Swan St., San Diego, CA (US) 92114; John A. Malo, 8661Lepus Rd., San Diego, CA (US) 92126

( * ) Notice: Subject to any disclaimer, the term of this patent is extended or adjusted under 35 U.S.C. 154(b) by 0 days.

(21) Appl. No.: 09/566,800

(22) Filed: May 8, 2000

Related U.S. Application Data

(63) Continuation-in-part of application No. 09/549,041, filed on Apr. 13, 2000, and a continuation-in-part of application No. 09/566,800, filed on May 1, 2000.

(51) Int. Cl.
*G06F 15/16* (2006.01)
(52) U.S. Cl. .................. 709/246; 709/224; 709/227; 709/206; 709/200; 714/43; 365/195; 345/764
(58) Field of Classification Search ............... 709/227, 709/206, 200, 224, 246; 714/43; 345/764; 365/195; 705/41
See application file for complete search history.

(56) References Cited

U.S. PATENT DOCUMENTS

| | | | | |
|---|---|---|---|---|
| 4,216,462 A | * | 8/1980 | McGrath et al. ........... | 600/301 |
| 5,396,613 A | * | 3/1995 | Hollaar ...................... | 714/4 |
| 5,875,242 A | * | 2/1999 | Glaser et al. ........... | 379/201.05 |
| 6,018,721 A | * | 1/2000 | Aziz et al. ................ | 705/36 R |
| 6,076,107 A | * | 6/2000 | Chen et al. .................. | 709/224 |
| 6,105,008 A | * | 8/2000 | Davis et al. .................. | 705/41 |
| 6,167,438 A | * | 12/2000 | Yates et al. .................. | 709/216 |
| 6,198,783 B1 | * | 3/2001 | Campana, Jr. ............... | 375/346 |
| 6,219,691 B1 | * | 4/2001 | Youn ......................... | 709/200 |
| 6,256,676 B1 | * | 7/2001 | Taylor et al. ................ | 709/246 |
| 6,375,469 B1 | * | 4/2002 | Brown ........................ | 434/236 |
| 6,415,318 B1 | * | 7/2002 | Aggarwal et al. ........... | 709/206 |
| 6,442,588 B1 | * | 8/2002 | Clark et al. .................. | 709/203 |
| 6,477,646 B1 | * | 11/2002 | Krishna et al. .............. | 713/189 |
| 6,600,683 B2 | * | 7/2003 | Yamane ...................... | 365/195 |
| 6,621,505 B1 | * | 9/2003 | Beauchamp et al. ........ | 345/764 |
| 6,654,914 B1 | * | 11/2003 | Kaffine et al. ................ | 714/43 |
| 6,658,260 B2 | * | 12/2003 | Knotts ........................ | 455/466 |

* cited by examiner

*Primary Examiner*—Thanh Tammy Nguyen
(74) *Attorney, Agent, or Firm*—Kacvinsky LLC

(57) ABSTRACT

A network apparatus is provided that may include one or more security accelerators. The network apparatus also includes a plurality of network units cascaded together. According to one embodiment, the plurality of network units comprise a plurality of content based message directors, each to route or direct received messages to one of a plurality of application servers based upon the application data in the message. According to another embodiment, the plurality of network units comprise a plurality of validation accelerators, each validation accelerator to validate at least a portion of a message before outputting the message.

7 Claims, 11 Drawing Sheets

SCALABLE NETWORK APPARATUS FOR CONTENT BASED SWITCHING OR VALIDATION ACCELERATION

CROSS-REFERENCE TO RELATED APPLICATIONS

This application is a continuation-in-part (CIP) of prior U.S. application Ser. No. 09/549,041 filed Apr. 13, 2000, entitled "A Network Apparatus For Switching Based On Content Of Application Data", having the inventor(s) John B. Abjanic, and is a CIP of prior U.S. application Ser. No. 09/566,800 filed May 1, 2000, entitled "A Network Apparatus For Validating Documents", having the inventor(s) David A. Marlatt and John B. Abjanic, the subject matter of all such applications being incorporated herein by reference.

FIELD

The invention generally relates to computers and computer networks and in particular to a scalable network apparatus which may be cascaded together to accommodate increased traffic.

BACKGROUND

While increasingly more successful in their roles as store and forward data systems, computer networks such as the Internet are experiencing tremendous growth as transaction-based, mission critical business applications, Web site owners, and business servers are overwhelmed by explosive traffic growth. The traditional approach is to buy more servers and network bandwidth. There is typically no distinction between levels of service, but rather a first-in first-out (FIFO) best efforts approach has been the default. However, this has resulted in uneven performance and undifferentiated service. Clearly, there is a need for a technique to allow service providers to intelligently offer different services and different levels of service depending on the circumstances.

Systems are available that allow messages to be routed based upon headers or header information. For example, in Hypertext Transfer Protocol (HTTP), a Post request method includes a request line, a header (or one or more headers) and a body. The request line includes a pointer to a requested resource or program to process the message, such as a Universal Resource Identifier (URI) or Universal Resource Locator (URL). The HTTP header may also include the type of message, the length of the body, and the date. There are systems that parse or examine the URL (i.e., the request line) and/or the HTTP header, and then route the message to a destination node based on the URL and/or header. One such system is described in "The Advantages of F5's HTTP Header Load Balancing Over Single-Point URL Parsing Solutions." However, this approach is very limited as switching decisions are based only on the HTTP header and/or URL.

XML, or eXtensible Markup Language v. 1.0 was adopted by the World Wide Web Consortium (W3C) on Feb. 10, 1998. XML provides a structured syntax for data exchange. XML is a markup language, like HTML. Most markup languages, like HTML, are fixed markup languages. That is, the fixed markup languages (including HTML) include a set of fixed tags for crafting a document. On the other hand, XML does not define a fixed set of tags, but rather, only defines a syntax or structured format through which users can define their own set of XML tags. There presently are a number of XML based languages which define their own set of tags using the XML syntax. XML has the further advantage because the actual data is separated from the presentation of the data, in contrast with HTML which combines these two items. As a result, XML has the potential to become a standard by which most computers, servers and applications will exchange or communicate data.

Another system, known as BizTalk™, improves slightly on the URL parsing technique by providing a system that is compatible with XML-based messages. As described in "BizTalk Framework 1.0a Independent Document Specification," Microsoft Corp., Jan. 7, 2000, BizTalk defines a specific set of tags (or BizTags) within a message that are used to specify business document handling (p. 7). A Biztalk server uses information contained in the Biztags to determine the correct transport-specific destination address(es). (pp. 9, 11). However, the tags used to mark up business transaction information within the message body are determined by the individual implementation. These implementation-specific tags (provided in the content or business transaction information of the message body) are not considered BizTags (p. 11). The BizTalk system is very limited because it can route or switch messages based only upon header or introductory information, based upon the fixed set of the BizTalk tags. The BizTalk system does not make decisions or route/switch messages based upon the actual content of the application data or business information (e.g., business transaction information) within the message body. Moreover, performing such processing at an application server can inhibit or decrease the number of documents or transactions that can be processed by the application server In addition, the XML standard only requires that a received document be checked to confirm that it meets the basic syntax and format of XML (i.e., determine whether the document is "well formed"). In addition, the XML standard also allows a document to be validated, which is a more rigorous check to determine if the structure or grammar of the XML document complies with structure required by the particular XML based language. Although not required by the XML specification, many application servers or other processing nodes that process XML documents include a validating XML processor (or a validating XML parser) to check the XML application data for validity against a validation template. As a result, the burden of performing document validation can also significantly decrease the number of documents or transactions that can be processed by the application server or processing node.

BRIEF DESCRIPTION OF THE DRAWINGS

The foregoing and a better understanding of the present invention will become apparent from the following detailed description of exemplary embodiments and the claims when read in connection with the accompanying drawings, all forming a part of the disclosure of this invention. While the foregoing and following written and illustrated disclosure focuses on disclosing example embodiments of the invention, it should be clearly understood that the same is by way of illustration and example only and is not limited thereto. The spirit and scope of the present invention is limited only by the terms of the appended claims.

The following represents brief descriptions of the drawings, wherein.

DETAILED DESCRIPTION

I. Content Based Switching

Figure 1:
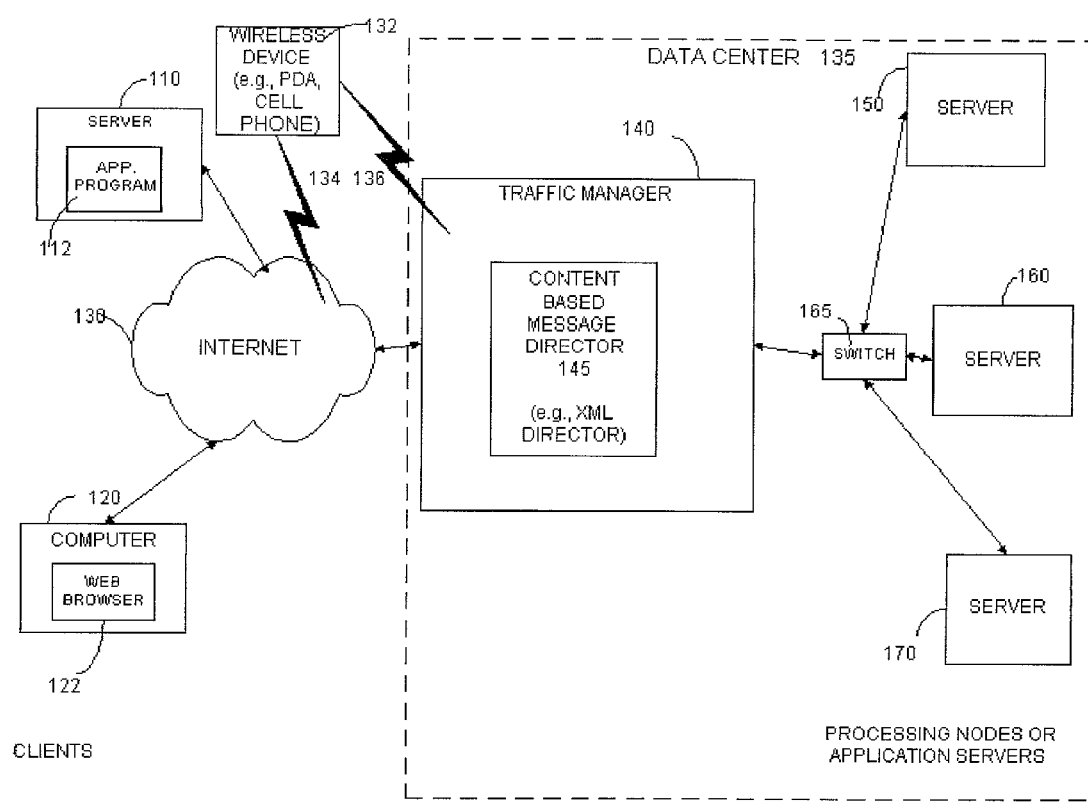
FIG. 1 is a block diagram of a network system according to an example embodiment.

Referring to the Figures in which like numerals indicate like elements, FIG. 1 is a block diagram of a network system according to an example embodiment. As shown in FIG. 1, a variety of clients may be coupled or connected to a data center 135 via a network, such as the Internet 130. The clients, for example, may include a server 110 that includes an application program 112, a computer 120 (such as a personal computer or laptop) that may include a web browser 122 and a wireless device 132, such as a personal digital assistant (PDA) or a wireless (or cellular) telephone. Wireless device 132 may be coupled to the Internet 130 or to a data center 135 via communications links 134 and 136, respectively. Links 134 and 136 each may include one or more of a wireless link (e.g., cellular or other link) or a wireline link. Each of the clients, including server 110, computer 120 and device 132 can send and receive messages over the Internet 130 and may use a variety of different protocols or transports.

The data center 135 is provided for sending, receiving and processing a wide variety of messages, requests, business transactions, purchase orders, stock quotes or stock trades, and other information. The data center 135 includes several processing nodes (e.g., servers), including server 150, server 160 and server 170 for handling the various orders, business transactions and other requests. The different servers in data center 135 may be allocated to provide different services, or even different levels of services. According to an example embodiment, the clients and the data center 135 exchange business transaction information or other information by sending and receiving XML messages (data provided in XML or in a XML based language), or messages based upon another type of structured syntax for data interchange.

The various servers (e.g., servers 150, 160 and 170) are coupled to a traffic manager 140 via a switch 165. Traffic manager 140 may perform a variety of functions relating to the management of traffic, including load balancing (e.g., balancing the load of incoming messages or requests across the available servers according to some policy, such as round-robin, least number of connections, or other load balancing technique).

Referring to the clients again in FIG. 1, application program 112 may be a business program or a program for managing inventory, orders or other business transactions. For example, application program 112 may automatically and electronically detect that inventory has decreased below a threshold value and then automatically generate and send a purchase order to a supplier's server at data center 135 to request a shipment of additional supplies or inventory. Thus, server 110 may initiate, for example, a business-to-business (B2B) transaction by sending an electronic order to the supplier's remote server located at data center 135.

As a another example, web browser 122 may request web pages, business information or other information from a remote server (e.g., located at data center 135). Web browser 122, may also send or post purchase orders, business transactions or other business information to a remote server, which may be located at data center 135. Wireless device 132 may receive information or data related to purchase orders, business transactions, web pages, stock quotes, game scores and the like from one or more remote servers (such as servers located at data center 135).

According to an embodiment, the server 110, computer 120 and wireless device 132 each may communicate or interchange data with one or more remote servers (e.g., servers 150, 160 and 170) by sending and receiving XML data (i.e., application data that is encoded or formatted according to the XML standard or according to one or more XML based languages).

According to an example embodiment, the traffic manager 140 includes a content based message director 145 to direct or switch messages to a selected server based upon the content of application data, such as business transaction information (which may be provided as XML data). Traffic manager 140 and/or message director 145 may be software, hardware or a combination of both, and may even be provided on or as part of a network processor. It should be noted that director 145 may operate by itself, or as part of a larger network apparatus, such as part of a traffic manager 140.

According to an example embodiment, because of the advantages of XML, application data can advantageously exchanged between the servers of data center 135 and one or more clients or computing nodes by sending and receiving messages that include application data that is encoded or formatted according to the XML standard. Therefore, according to an embodiment, director 145 may be a XML director because it directs (or routes/switches) the incoming message to a particular server based upon the XML data in the message. The XML data preferably complies with the format or syntax required by the XML standard. A document that uses tag formats (e.g., start tags, end tags) and other syntax (e.g., to markup data) that complies with the XML standard is considered to be a "well-formed" XML document.

Therefore, in an exemplary embodiment, content based message director 145 is a XML director. However, it should be understood that director 145 can direct or switch messages having basically any type of structured syntax, including any type of markup language.

An advantageous aspect of the embodiment of the traffic manager 140 and director 145 shown in FIG. 1 is that the traffic manager 140 and the director 145 are located in front of the one or more application servers or processing nodes. By locating the traffic manager 140 and director 145 in a computer, server or computing system in front of the processing nodes or servers (as shown in FIG. 1) (e.g., coupled between the network 130 and the servers), the traffic management functionality and the functionality of the director 145 can be off-loaded from an application server to a separate and/or dedicated network apparatus or network system. This can advantageously relieve the processing nodes or application servers from this additional processing overhead.

Figure 2:
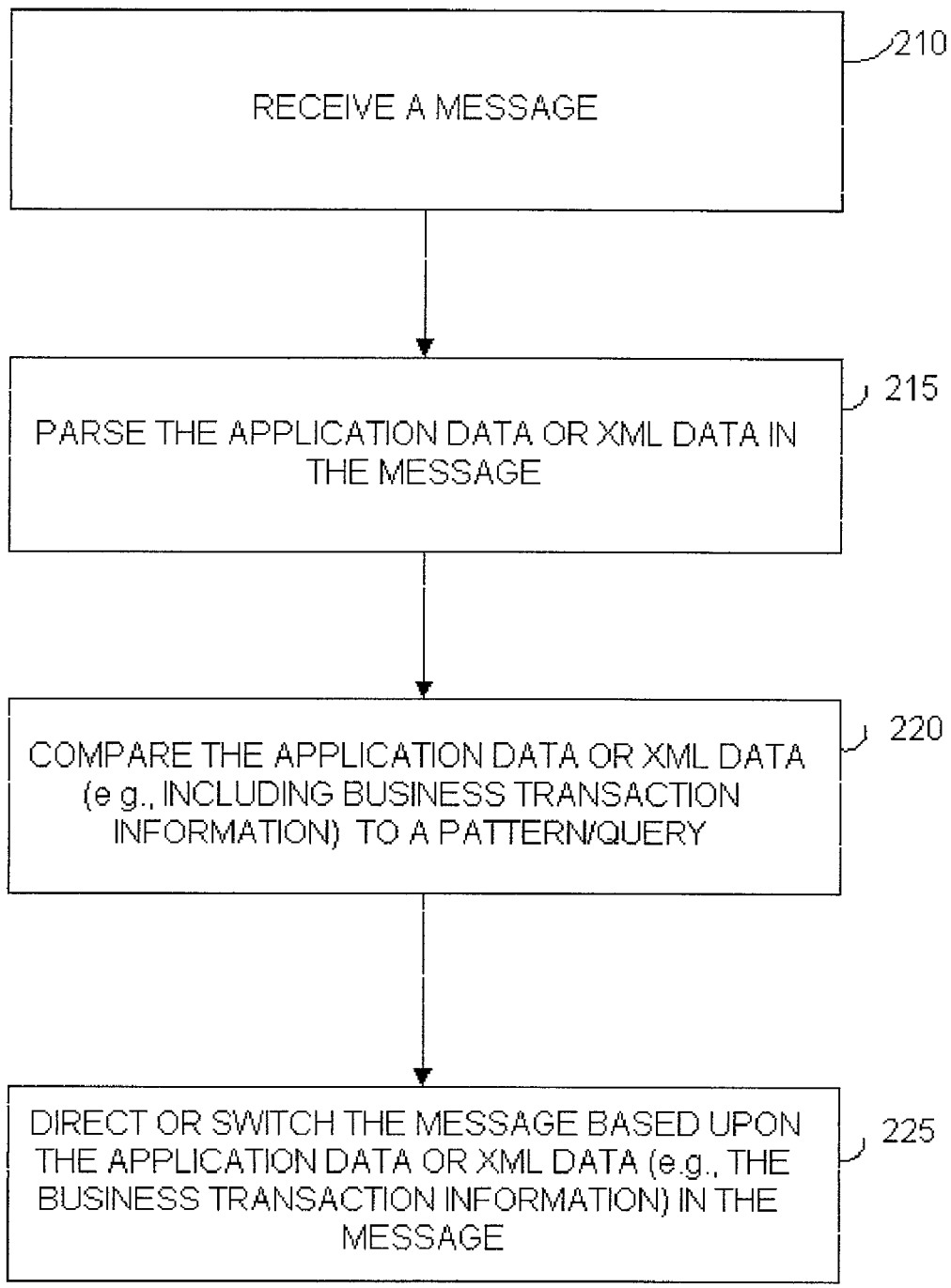
FIG. 2 is a flow chart illustrating an operation of content based message director according to an example embodiment.

FIG. 2 is a flow chart illustrating an operation of content based message director according to an example embodiment. At block 210, the director 145 receives a message. The message may be sent over any transport or protocol(s), such as Transmission Control Protocol (TCP), File Transfer Protocol (FTP), Simple Mail Transfer Protocol (SMTP), Wireless Application Protocol (WAP, which may be used to send and receive information with wireless devices), Hypertext Transfer Protocol (HTTP), etc. The general teachings and the operation of the invention are not dependent upon any particular transport or protocol, but rather are transport-independent.

A HTTP Post is an example of a message. The format for an HTTP Post message (or HTTP request) may be presented as:
request-line (the URL); identifies a program for processing the message headers (0 or more)
<blank line>
body (the application data or the XML data; only for a POST)
Here's an example:
POST www;acme.com/purchasing/order.cgi HTTP/1.1
Content-Type: text/xml
Content-Length: 1230
User-Agent: Cern-Line Mode/2.15
Date: 3/27/00
<XML>
  <From>intel.com</From>
  <To>bookstore.com</To>
  <PurchaseBook>
    <ISBN>02013798233</ISBN>
    <PurchaseAmount> 98</PurchaseAmount>
  </PurchaseBook>
</XML>

In this example, the URL (or request line) is provided in a request line to identify a program or application to process the message. Several header lines (Content-type, Content-length, date, etc.) make up an HTTP header. The application data is provided after the HTTP header, and in this example is provided as XML data. A start tag <XML>, and </XML>, an end tag, identify the start and end, respectively, of the application data (or XML data). This XML application data is also referred to as a XML document. The XML document includes markup characters (or tags) which describe data, and data characters. As an example, a "To" element of the above XML document is written as: <To>bookstore.com</To>. Where <To> is a start Tag and </To> is an end tag, which are markup characters because they describe the XML data characters (bookstore.com). The business transaction information describes the business transaction (To, From, items purchased, purchase amount, quantity, etc.), and is not included in the URL, the HTTP header, or any other header (e.g., IP header, TCP header) of the envelope used for sending the message.

While the prior art performed switching based on the request line or URL and/or the HTTP header, the present invention is directed to a technique to perform switching at a network apparatus based upon the application data, such as XML data (which includes business transaction information).

In this example message, the business transaction information provided within the application data as XML data relates to the transaction or describes the transaction, including, for example, what kind of business transaction (a purchase order or to purchase a book), who it is from and who it is to, an ISBN number to identify the goods to be purchased and the amount of the purchase (PurchaseAmount). These are merely examples of the types of business transaction information in a message upon which the director 145 can analyze and make routing or switching decisions for the message.

At block 215 of FIG. 2, the director 145 (FIG. 1) parses all or part of the application data (the XML data in this example) and can check to ensure that the XML document or application data is well formed (i.e., checks to make sure at least a portion of the XML document meets the so-called well-formedness constraints or requirements in the XML specification or standard). Parsing generally refers to the process of categorizing the characters or XML data that make up the XML document as either markup (e.g., <To>) or character data (e.g., bookstore.com).

At block 220 of FIG. 2, the application data or XML data (including markup characters and/or character data) is then compared to one or more configuration patterns or queries (which may be stored in the director 145) to determine if there is a match. According to an embodiment, the configuration patterns may be dynamically changed or updated by a user or by a program or application. For example, a program may detect the failure of one or more servers and/or detect the response time of servers, and then update the configuration pattern to account for these changes in the network (e.g., redirect certain messages from busy servers to servers which are less busy, or from servers which have failed to the available servers).

At block 225, if there is a match between the content of the application data (e.g., the business transaction information which may be provided as XML data) of a message and a configuration pattern or query, then the director 145 directs or switches the message to the corresponding server (or processing node) in the data center (e.g., directed to the specific server as indicated by the configuration pattern). If there are multiple matches, the director 145 can just direct the message based to the first match, or a load balancing policy can be used to balance messages among a group of servers. If there is no match, the message can be directed to a default server or can be blocked. Alternatively, the configuration pattern can also identify a certain pattern for which a message should be blocked from being forwarded. In this respect, the director 145 may also act as a filter to selectively pass or forward some messages while blocking others, based upon the application data.

For example, the director 145 may be configured to direct or switch messages based on the following configuration patterns or queries:

| Sever | IP address | Port | XML pattern |
|---|---|---|---|
| S1 (e.g., 150) | 10.1.1.1 | 80 | To = bookstore.com |
| S2 (e.g., 160) | 10.1.1.2 | 80 | To = stockquote.com |
| S3 (e.g., 170) | 10.1.1.3 | 80 | To = computerstore.com |

Based on the above configuration patterns, the director 145 would direct a message to server S1 (having the IP address 10.1.1.1 and port 80) if the data for the To element of the business transaction information is bookstore.com. The message will be directed to server S2 (having an IP address 10.1.1.2 and port 80) if the data for the To element of the business transaction information is stockquote.com. And, the director 145 will direct any messages to server S3 if the data for the To element of the business transaction information is computerstore.com.

This advantageously allows different types of services (or different levels of service) to be provided for messages based on the content of the application data (such as the business transaction information) in the message. In this example, server S1 may be allocated to handle purchase orders for books sent to bookstore.com. Server S2 may be allocated to process requests for real-time stock quotes, while server S3 may be allocated to process purchase orders for computers sent to computerstore.com.

There are many examples where content based switching based upon the content of the application data or business transaction information can be used to offer different or differentiated services or even different or differentiated levels of services. As another example, the director 145 may be configured to direct or switch messages based on the following configuration patterns or queries:

| Sever | IP address | Port | XML pattern |
|---|---|---|---|
| S1 (e.g., 150) | 10.1.1.1 | 80 | PurchaseAmount < $100 |
| S2 (e.g., 160) | 10.1.1.2 | 80 | $100 < PurchaseAmount < $1000 |
| S3 (e.g., 170) | 10.1.1.3 | 80 | $1000 < PurchaseAmount |
| S4 (not shown) | 10.1.1.4 | 80 | $1000 < PurchaseAmount |

In this example, messages for purchase orders are sent to server S1 if the purchase amount is less than $100; messages for purchase orders are sent to S2 if the purchase amount is less than $1000 and more than $100; and for the high dollar purchases, the messages for purchase orders for purchases greater than $1000 can be sent to either of two servers. In this fashion, the director 145 (FIG. 1) can direct or route received messages based on the content of the application data or business transaction information in the message. This allows web sites or electronic-businesses (e-businesses) to offer different or differentiated levels of services based on the content of the application data or transaction information.

In this particular example, two servers (S3 and S4) have been allocated to handle the highest dollar purchase orders. Thus, by specifically allocating greater resources (e.g., two or more servers as compared to just one server) for the higher dollar amount purchases as compared to the lower dollar purchases, an e-business operating at data center 135 can provide a higher level of service for purchase order messages having a higher dollar purchase amount. In this manner, director 145 can switch or direct messages to another network device or to a specific server based upon a wide variety of business transaction information or application data.

Figure 3:
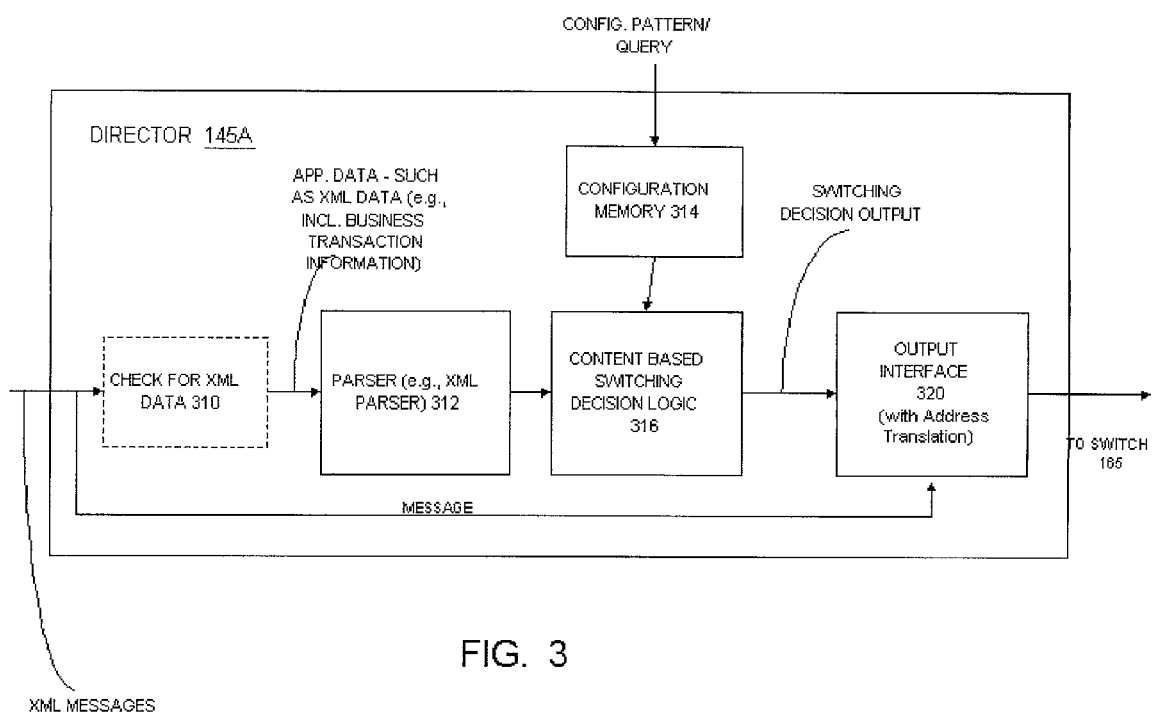
FIG. 3 is a block diagram illustrating a director according to an example embodiment.

FIG. 3 is a block diagram illustrating a director according to an example embodiment. Director 145A includes a block 310 to determine whether a received message includes XML data.

According to an embodiment, if the message does not include XML data, the message will be passed (e.g., directly) through to the output with little if any further processing by director 145A. If the message does include XML data, then the message will be analyzed for making a routing or switching decision as described below.

There are many ways in which block 310 can determine whether a received message includes XML data. According to one embodiment, certain types of filenames (e.g., invoice.cgi) or filename extensions (e.g., *.cgi), which may typically be provided in the request line, may indicate whether the message includes XML data. Thus, the filename extension may be analyzed by block 310 to determine whether the message includes XML data. Other information in the message, including other header information or even a particular tag in the application data itself (e.g., the <XML> start tag) can be used to identify whether or not the message includes XML data.

According to an embodiment, block 310 is optional. However, it is advantageous to provide block 310 where only a small percentage of the incoming messages include XML data. Without block 310, application data for all messages will be parsed and compared to the configuration pattern, and a switching decision will be generated. Thus, for those messages which do not include XML data (and thus cannot be switched or directed by director 145A), director 145A will add unnecessary latency in the message forwarding path in the absence of block 310. On the other hand, where a significant percentage of the messages received by director 145A include XML data, block 310 may be considered unnecessary and may be omitted (because block 310 would typically add unnecessary latency in such case).

A parser 312 is coupled to the output of the block 310 to parse the application data (or a portion thereof). A configuration memory 314 receives and stores one or more configuration patterns or queries. A content based switching decision logic 316 receives the output from the parser 312 and compares the configuration patterns to the application data or business transaction information (e.g., including the data and the markup characters describing the data within the configuration pattern). The content based switching decision logic 316 then outputs a switching or routing decision for the message on the basis of the comparison (i.e., on the basis of the business transaction information). The configuration pattern may indicate both a pattern and a processing node or server to process the message if a pattern is found in the message.

The output interface 320 then switches or directs the message on the basis of this decision (e.g., routes the message to the processing node or server indicated by the matching configuration pattern). For example, if there is no match, the output interface 320 may filter or block the message, or may direct or route the message to a default server or a predetermined server in the data center 135. If a match is found, the output interface 320 switches or directs the message to the appropriate destination (e.g., to the appropriate processing node or server within data center 135).

The configuration pattern may require multiple patterns, or even a hierarchical arrangement of data elements in the application data for a specific match. For example, the decision logic 316 may receive a configuration pattern that specifies:

| Server | IP address | XML pattern |
|---|---|---|
| S1 (e.g., 150) | 10.1.1.1 | From = Intel; and PurchaseAmount < $100 |

In such a case, the switching decision logic 316 would examine the application data (or XML data) to first identify a From tag that is set to Intel. Next, it would examine the transaction information to identify a PurchaseAmount that is less than $100. If both of these are found, this indicates a match.

If a match is found between the business transaction information and the pattern, the content based switching logic 316 outputs a switching decision to a output interface 320. The switching decision may, for example, indicate that a match was found and identify the processing node or server (e.g., by address and port number or other identifier) where the message should be directed.

According to an example embodiment, the decision logic 316 provides an IP address and port number to be used as a new destination IP address and destination port number for the message. The output interface 320 may then translate the destination IP address and port number in the packet or envelope of the received message from the original destination IP address and port number (i.e., the IP address and port number of the traffic manager 140 or director 145A) to the new destination IP address and port number provided by the decision logic 316. According to an embodiment, the new destination IP address identifies a processing node or server (e.g., within data center 135 or elsewhere) and the new destination port number identifies a program or application on that processing node or server that will receive and process the message.

The message (e.g., with its associated TCP and IP headers translated or modified to include the new destination address and port number) is then output from the director 145 and traffic manager 140. Switch 165 receives the message, and then routes the message to the appropriate processing node or server based on the IP address.

According to an example embodiment, a client (e.g., a server 110, computer 120, etc., FIG. 1) that sends a message first establishes a connection (e.g., a TCP connection), and then sends the message via HTTP (or other transport) to the traffic manager 140 and/or director 145A. The director 145A then parses the XML data, and makes a switching decision based on the business transaction information in the message as compared to one or more configuration patterns. A new connection is then established between the director 145A or traffic manager 140 and the destination processing node or server. The message is then directed or routed from director 145A to the specified node or server.

Figure 4:
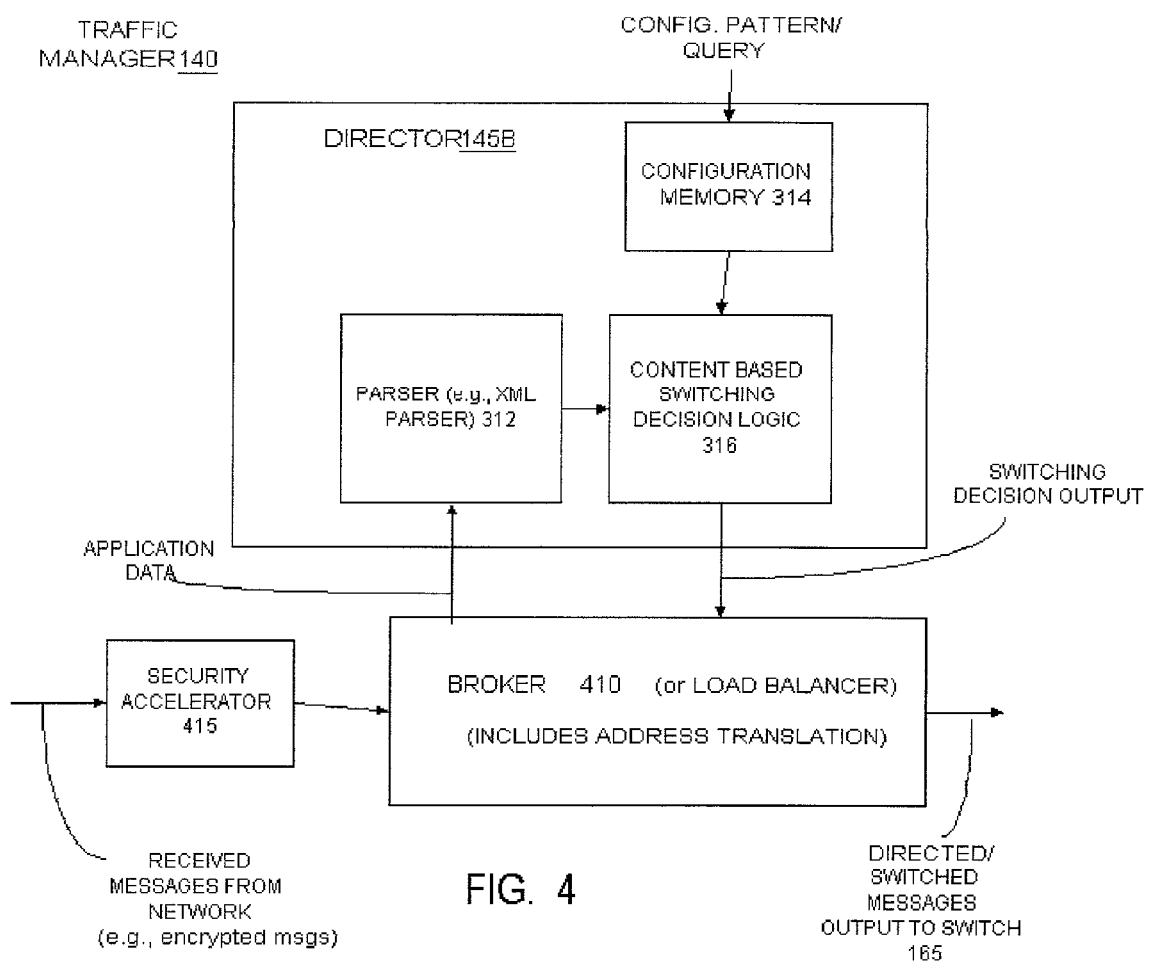
FIG. 4 is a block diagram illustrating a traffic manager according to another example embodiment.

FIG. 4 is a block diagram illustrating a traffic manager according to another example embodiment. Traffic manager 140 includes a security accelerator 415 for encrypting outgoing messages and/or decrypting incoming messages received from the network. According to an embodiment, the security accelerator 415 is a Secure Sockets Layer (SSL) accelerator, available from Intel Corporation. The security accelerator 415 allows the security related tasks such as encryption and/or decryption to be off-loaded from the application server to the accelerator 415 of the traffic manager 140.

Traffic manager 140 also includes a director 145B and a broker 410. A decrypted message is received by broker 410 from security accelerator 415. According to an example embodiment, broker 410 operates as both an output interface (similar to output interface 320) and a load balancer to balance or adjust the traffic among one or more of servers or processing nodes within the data center 135.

Director 145B is similar to director 145A but may not include block 310 and/or the output interface 320 of director 145A (as these functions may be provided by the broker 410 in FIG. 4). Parser 312 (which may be optional) parses the XML data. The content based switching decision logic 316 compares the configuration patterns to the application data or business transaction information in the message and then outputs a switching decision to broker 410 for the message on the basis of the comparison. The switching decision output to broker 410 may, for example, identify the IP address and port number of the selected processing node or server or application server that should receive the message.

Broker 410 performs address translation on the header(s) for the message. The address translation performed by broker 410 includes a destination address and destination port translation and an optional source address and source port translation. The destination address and port translation may be performed by translating the original destination IP address and port number of the received message (which may identify the broker 410) to the IP address and port number of the specified processing node or server (or of the specified server resource or program). In addition, the broker may also translate the source IP address and port number in the packet or envelope from the originating client's address and port number to the IP address and port number of the broker 410 (or of the traffic manager 140). The message (including one or more translated addresses) is then output from broker 410. Switch 165 (FIG. 1) receives the message and forwards the message to the appropriate server based on the destination address in the message. According to one embodiment, it is not necessary to actually translate the source IP address and port number if all return messages or replies from the processing node or server are routed through the broker 410.

Broker 410 also translates destination addresses for return messages or replies from the processing node or server sent to the client, to substitute the IP address and port number of the client as the destination address and port for the return message or reply. Thus, the broker 410 may operate as a gateway or output interface between the client (FIG. 1) and the processing node or server, by performing destination address translation prior to routing or forwarding the message, and performing a similar translation for return or reply messages sent from the processing node or server back to the client.

According to an example embodiment, broker 410 and security accelerator 415 may be provided, for example, as an Intel® NetStructure™ 7180 E-Commerce Director. Alternatively, the broker 410 may be provided as an Intel® NetStructure™ 7170 Traffic Director. Both are available from Intel Corporation, Santa Clara Calif. As a result, broker 410 may perform additional functions including load balancing according to a load balancing policy or algorithm to adjust the load on each server in the data center.

The director 145 (or 145A or B), the security accelerator 415 and the broker 410 (or load balancer) may be provided in a network apparatus in different combinations, depending on the circumstances.

Figure 5:
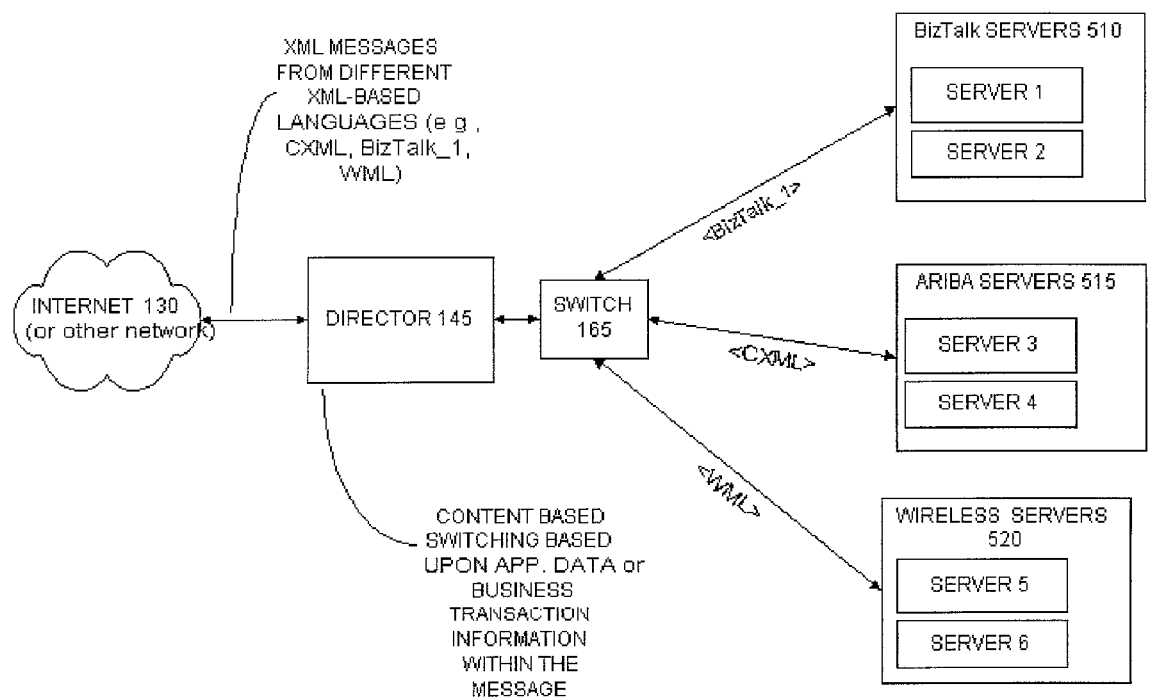
FIG. 5 is a block diagram illustrating another example operating environment for a content based message director according to an example embodiment.

FIG. 5 is a block diagram illustrating another example operating environment for a content based message director 145 according to an example embodiment. As noted above, XML does not define a fixed set of tags, but rather, only defines a syntax or structured format through which users can define their own set of tags or their own XML based language. In fact there are many different XML-based languages in use, each having a unique set of tags that define what elements should be provided to comply with that XML language.

An XML language can be defined by a validation template (indicating the proper form for the tags), known in XML as a Document Type Definition (DTD). Schemas can also be used. For example, BizTalk by Microsoft Corp. includes one set of XML tags; CXML by Ariba Corp. includes its own set of tags; CBL by Commerce One includes another set of XML tags; While WML (Wireless Markup Language) defines yet another set of XML tags for the communication or interchange of data to and from a wireless device. Each of these XML-based languages includes a different or unique set of tags, and thus each is generally incompatible with the other languages. For example, a client sending data using CXML will not be able to properly communicate with a processing node or server that expects to receive data only provided according to WML.

According to an advantageous aspect of the present invention, director 145 can receive an XML message, compare the application data or business transaction information to the configuration pattern, and then direct or route the message (or make switching or routing decisions) to an appropriate processing node or server regardless of the type of XML-based language used by the message. Once the director 145 is configured to detect or recognize one or more specific tags and corresponding data (e.g., PurchaseAmount>$100), the director 145 can direct or route the message based on the content of the application data (e.g., based on the business transaction information provided as XML data), regardless of the type of XML-based language that is used by the message.

As shown in FIG. 5, Director 145 is coupled to switch 165. There are three sets of servers (or data centers) coupled to the switch 165, including: a set of BizTalk servers 510 (including servers 1 and 2) which communicate data using an XML based language known as BizTalk; a set of Ariba servers 515 (including servers 3 and 4) which communicate data using the XML based language known as CXML; and a set of wireless servers 520 (including servers 5 and 6) which communicate data using only the XML based language known as Wireless Markup Language or WML. These are merely provided as examples. Thus, the director 145 can operate as a gateway or interface, receiving messages from a variety of different clients using a variety of different XML based languages, and then directing or routing the messages to the appropriate processing node or servers.

II. Validation Acceleration

Figure 6:
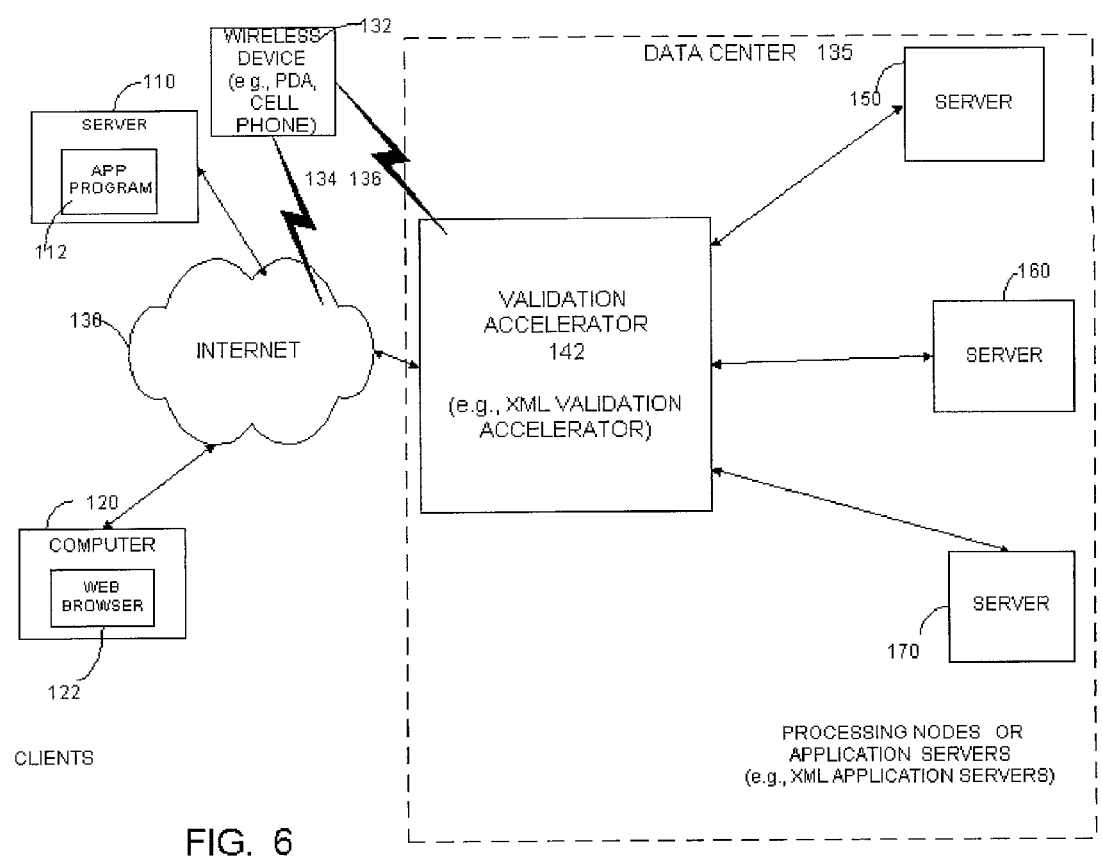
FIG. 6 is a block diagram illustrating a network system according to another example embodiment.

FIG. 6 is a block diagram illustrating a network including a validation accelerator 142 according to an example embodiment. According to an advantageous embodiment, the data center 135 also includes a validation accelerator 142 to pre-validate received messages before the messages are sent to one of the application servers or processing nodes. According to an example embodiment, the validation accelerator 142 is provided as a network apparatus. In other words, according to an example embodiment, the validation accelerator 142 can be coupled between a network 130 and a plurality of processing nodes or application servers (e.g., servers 150, 160 and 170). Providing the validation accelerator 142 as a network apparatus (i.e., separate from the application servers) allows the computationally expensive task of document validation to be off-loaded from the application servers to the validation accelerator 142. Alternatively, a plurality of validation accelerators 142 may be provided, with one validation accelerator 142 being provided for one or more application servers or other processing nodes.

As noted above, an XML document must be checked to ensure it meets the basic syntax and format of XML (i.e., determine whether the document is "well formed"). In addition, the XML standard also optionally allows a document to be validated, which is a more rigorous check to determine if the structure or grammar of the XML document complies with structure or grammar required by the particular XML based language. XML allows a document to be validated against a validation template. A validation template defines the grammar and structure of the XML document (including required elements or tags, etc.).

There can be many types of validation templates such as a document type definition (DTD) in XML or a schema, as examples. These two validation templates are used as examples to explain some features according to example embodiments. Many other types of validation templates are possible as well. A schema is similar to a DTD because it defines the grammar and structure which the document must conform to be valid. However, a schema can be more specific than a DTD because it also includes the ability to define data types (e.g., characters, numbers, integers, floating point, or custom data types). In addition, unlike a DTD (under present standards), a schema may be required to be well formed. Thus, both the application data and the schema can both be parsed and checked for basic syntax (or well-formedness). Therefore, at least for some applications, it is expected that schemas will possibly become more common than DTDs in the future.

As noted above, validating a received document against a validation template is optional according to the XML standard. If a document is to be validated against a particular validation template, the XML document will include validation instructions (or validation code) at the beginning of the document. One example of validation instructions can be a document type declaration, as commonly known in XML. Another example is a schema (or a reference to an external schema). According to current XML, the validation instructions (e.g., document type declaration or schema, etc.) is an optional area of the document that declares the structure, element types, attributes, etc. of the validation template. To be a valid document, the structure and grammar of the application data in the document must match the structure and grammar defined by the validation template (if validation instructions are included in the document). The validation template can be provided internal to (or within) the document and/or external to the document.

Figure 7:
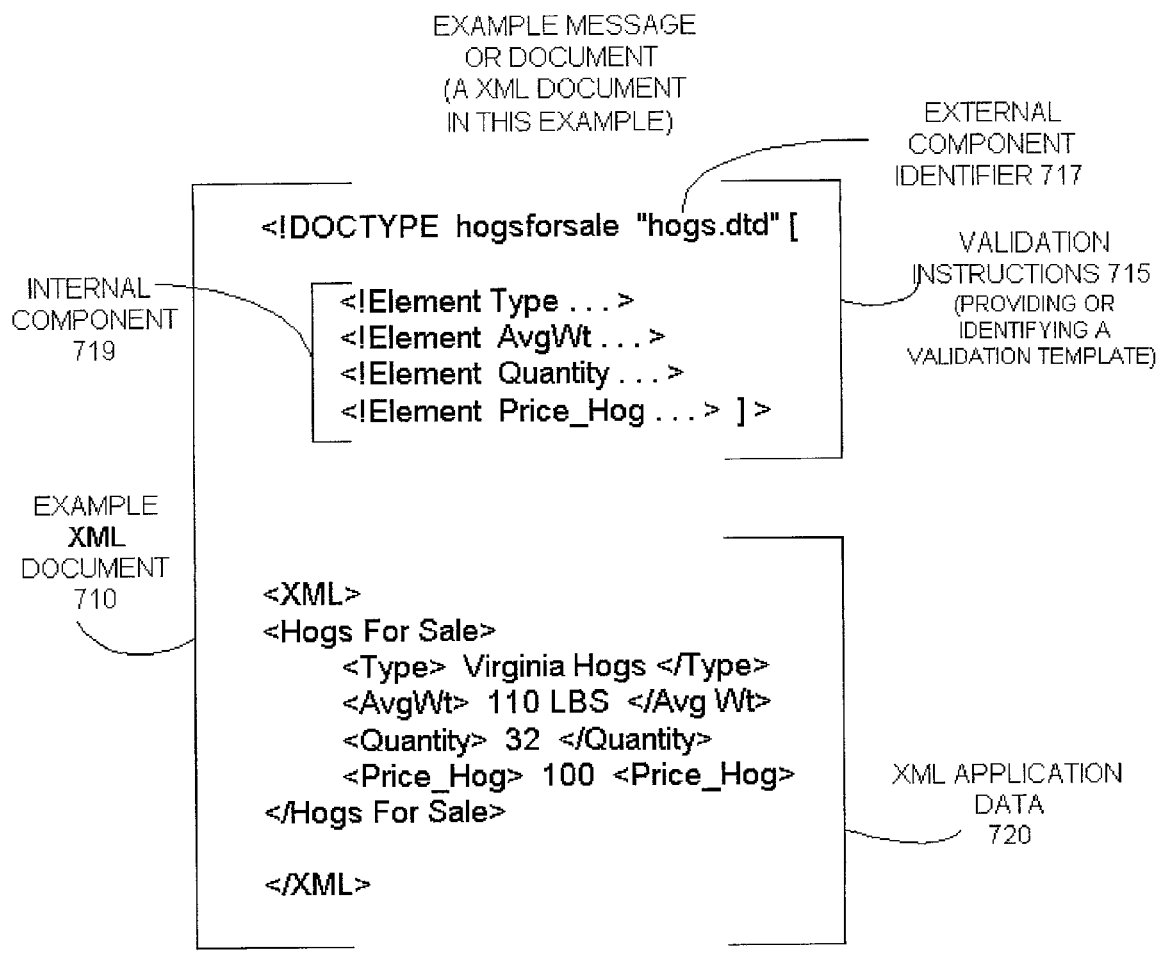
FIG. 7 is a diagram illustrating an example message according to an example embodiment.

FIG. 7 is a diagram illustrating an example message according to an example embodiment. The example message shown in FIG. 7 includes an XML document 710. XML document 710 includes XML application data 720 (e.g., including business transaction information) and validation instructions 715.

The application data 720 is the application data that will be processed by an application server. The application data 720 may include, for example, business transaction information, such as a list items to be purchased, prices, quantities or other specific details of a transaction or a request for information (e.g., request for stock quote, transaction details).

According to an embodiment, the presence of one or more validation instructions 715 indicates that the document can (or should) be validated before processing the application data 720 based on a validation template provided within and/ or identified by the validation instructions 715. In other words, according to an embodiment, the presence of validation instructions may indicate that the application data should be pre-validated at a network apparatus (such as validation accelerator 142) before passing the data to an application server for further processing. To indicate to the application server that the document (or the application data) has been validated, the validation instructions may be removed from the document and/or an indication (such as a comment or instruction in the data or a field set in the message) may be provided to indicate that the application data or message has been validated (i.e., pre-validated). According to current XML, document validation is optional (e.g., by the application server), even when validation instructions 715 are present. However, it is possible that in the future, validation (in XML or other languages) may be required.

If the document should be associated with a validation template (document type definition, schema, etc.) for document validation (i.e., to allow document validation), the document will typically include one or more validation instructions 715. The validation instructions 715 provide or identify the validation template (or document type definition) which defines the document structure and grammar (e.g., elements, attributes) to which the application data 720 of document 710 must conform. The validation template can include an internal component and/or an external component.

In this example shown (e.g., for XML), the validation instructions 715 (or validation template) are provided as a document type declaration. The validation instructions 715 begin with the DOCTYPE statement "<DOCTYPE hogsforsale . . . " which indicates that there is a validation template, which may be provided within the document (i.e., as internal component 719) or provided external to the document (i.e., an external component identified as "hogs.dtd"). Therefore, in this example, the validation instructions 715 provide an internal component 719 of a validation template and an external component identifier 717 identifying an external component. The internal component 719 and the external component (not shown) together form the validation template for this document (i.e., for validating the application data 720 for document 710). According to an embodiment, if validation is being performed, the presence of the DOCTYPE statement (or other validation instructions) typically will cause an application or application server to validate the application data 720 in the message against the validation template.

The internal component 719 of the validation template defines that a valid hosgsforsale document must include the following elements: type, avg wt, quantity and price/hog, etc. This is just an example.

In this example, the identifier "hogs.dtd" identifies an external entity or file which is an external component of the validation template. The external component can be located on a remote server or other location based on the external component identifier 717. The external component of the validation template (identified as "hogs.dtd") may include additional requirements on the structure or grammar of the application data 720 of the document 710. The external component identifier 717 may be provided as the complete address, or as a relative address or pointer (e.g., relative to the address or location of the source or originating node of the message). For example, the "hogs.dtd" identifier listed in the validation instructions 715 may actually reference the "hogs.dtd" external component 717 which may be found at (for example): oasis.xml.org/farming/livestock/hogs.dtd. As noted above, examples of validation templates include a Document Type Definition (e.g., for XML), a schema, etc.

Figure 8:
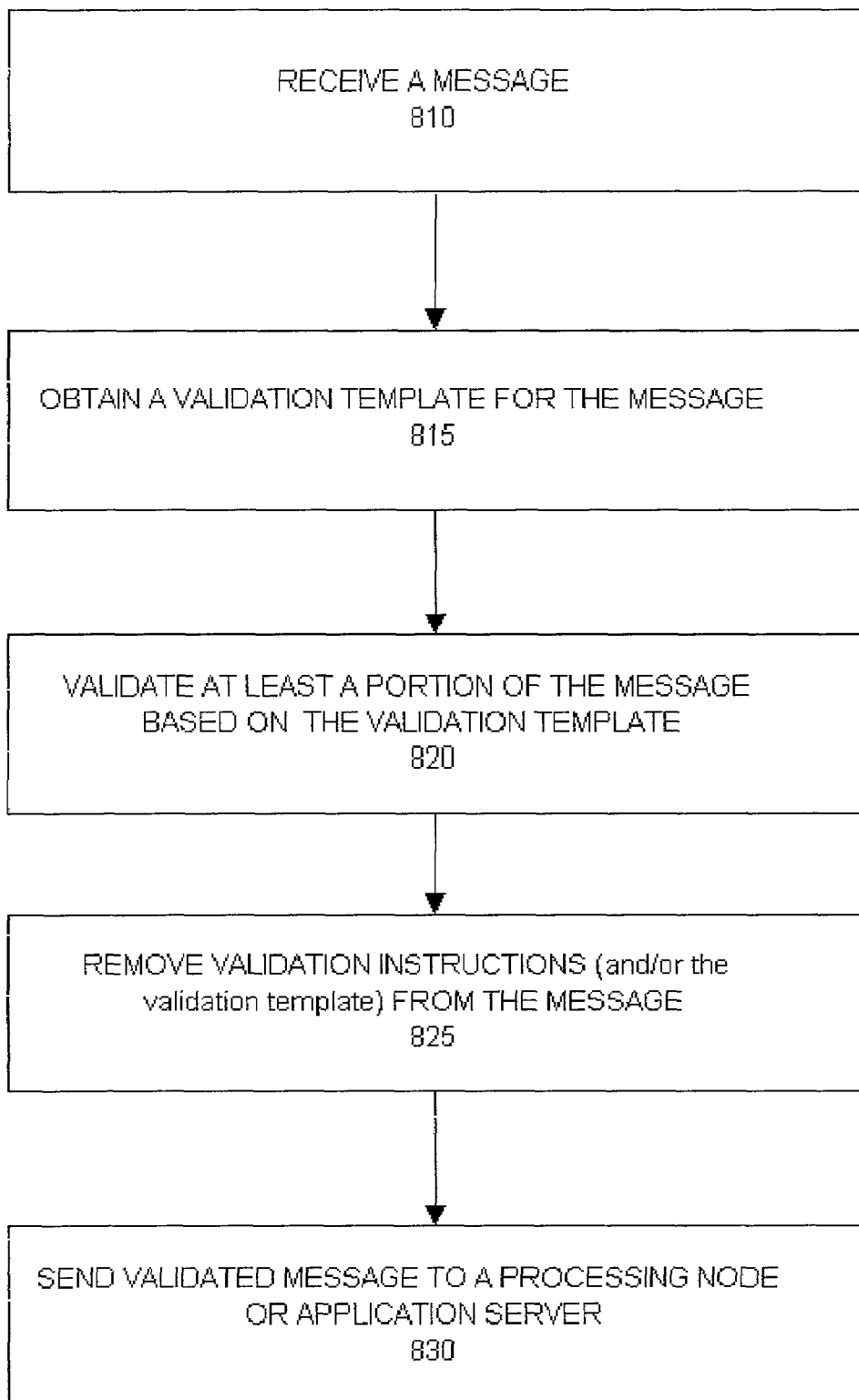
FIG. 8 is a flow chart illustrating an example operation of a validation accelerator according to an example embodiment.

FIG. 8 is a flow chart illustrating an example operation of a validation accelerator according to an example embodiment. At block 810, the validation accelerator 142 receives a message. The message may be sent over any transport or protocol (s), such as Transmission Control Protocol (TCP), File Transfer Protocol (FTP), Simple Mail Transfer Protocol (SMTP), Wireless Application Protocol (WAP, which may be used to send and receive information with wireless devices), Hypertext Transfer Protocol (HTTP), etc. The general teachings and the operation of the invention are not dependent upon any particular transport or protocol, but rather are transport-independent.

At block 815, a validation template is obtained by the validation accelerator 142 for validating the document or message (e.g., for validating the application data 720 in the document 710, FIG. 7). This may include first determining if validation instructions are present in the document or message. If no validation instructions are present, then validation will not be performed. If validation instructions are present, the validation accelerator 142 then determines whether the validation template for the document is provided as an internal component and/or an external component based upon the syntax of or one or more statements in the validation instructions 715.

If the validation template is provided within the document (i.e., as an internal component), the validation template is parsed from or separated from the remainder of the document. If the validation instructions 715 provide a external component identifier 717, then the validation accelerator 142 then retrieves or obtains the external component (e.g., from a remote server or node).

At block 820 of FIG. 3, the validation accelerator 142 validates at least a portion of the message (e.g., validates the application data 720) by comparing the structure and grammar of the application data 720 to the structure and grammar defined or required by the validation template.

At block 825, if the document or message is valid, the validation accelerator 142 then removes the (preferably all of the) validation instructions, including any statements that might cause the document to be validated (e.g., a DOCTYPE statement), any internal component(s) of the validation template and any references or identifiers to external components of the validation template.

At block 830, the validated document (with the validation instructions removed) is then sent to an application server or other processing node for processing.

Alternatively (or in addition to removing the validating instructions), an indication can be added to the message indicating to the application server that the application data or message has already been validated (i.e., pre-validated). This pre-validation indication can be provided, for example, as a field in the message, as an instruction or comment in the application data itself, or using another technique. For example, In the XML specification, besides element tags, and data, there is something known as a processing instruction tag which provides an "escape hatch" to allow information specific to an application to be embedded in an XML document. Processing instructions are not considered to be part of the character data content of an XML document, but they are always passed on to the XML application by the parser. The format is <? ......... ?> for the processing instruction tag. Thus, according to one embodiment, after the validation instructions (or the DTD or schema or reference thereto) has been removed, the following comment or instruction tag could be added near the beginning of the document (or other location): <? validated by intel ?>.

By pre-validating the document and then removing the validation instructions from the document (and/or adding a pre-validation indication to the document or message), the expensive step of validation is off-loaded from the application server to a network apparatus, network appliance or other system (which may be referred to, for example, as the validation accelerator 142).

Figure 9:
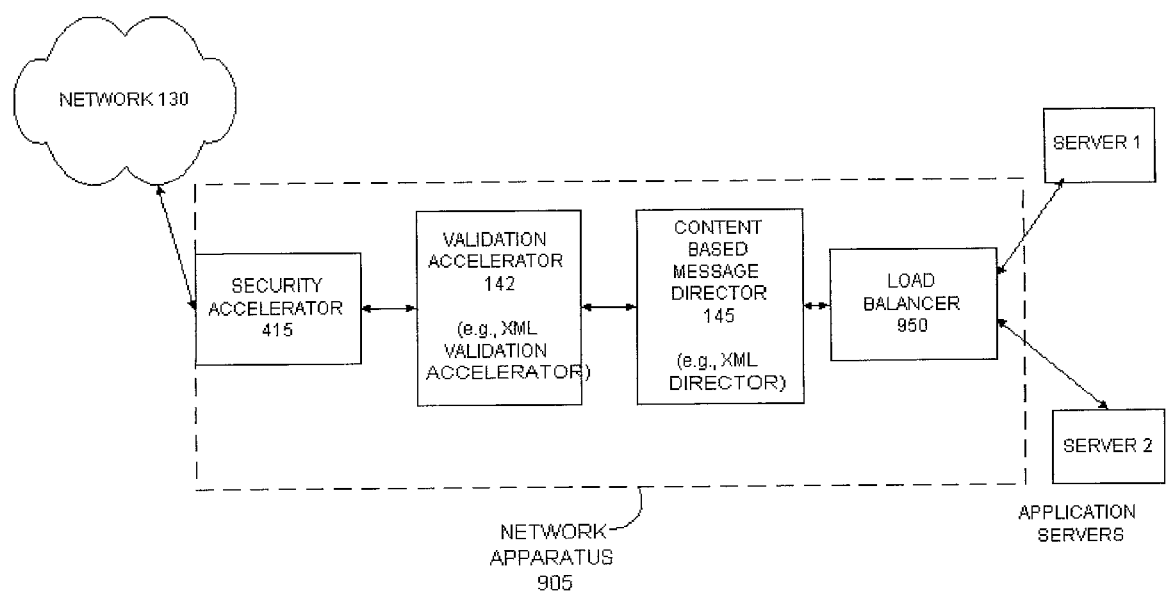
FIG. 9 is a block diagram illustrating a network apparatus according to another example embodiment.

FIG. 9 is a block diagram illustrating a network apparatus according to another example embodiment. According to an example embodiment, network apparatus 905 may include one or more of the blocks shown in FIG. 9. For example, in addition to the validation accelerator 142, a network apparatus 905 may include a security accelerator 415, a content based message director 145 and/or a load balancer 950. Alternatively, all four of the components can be provided in a network apparatus 905, or any sub-combination thereof.

III. Scalable Network Apparatus

Figure 10:
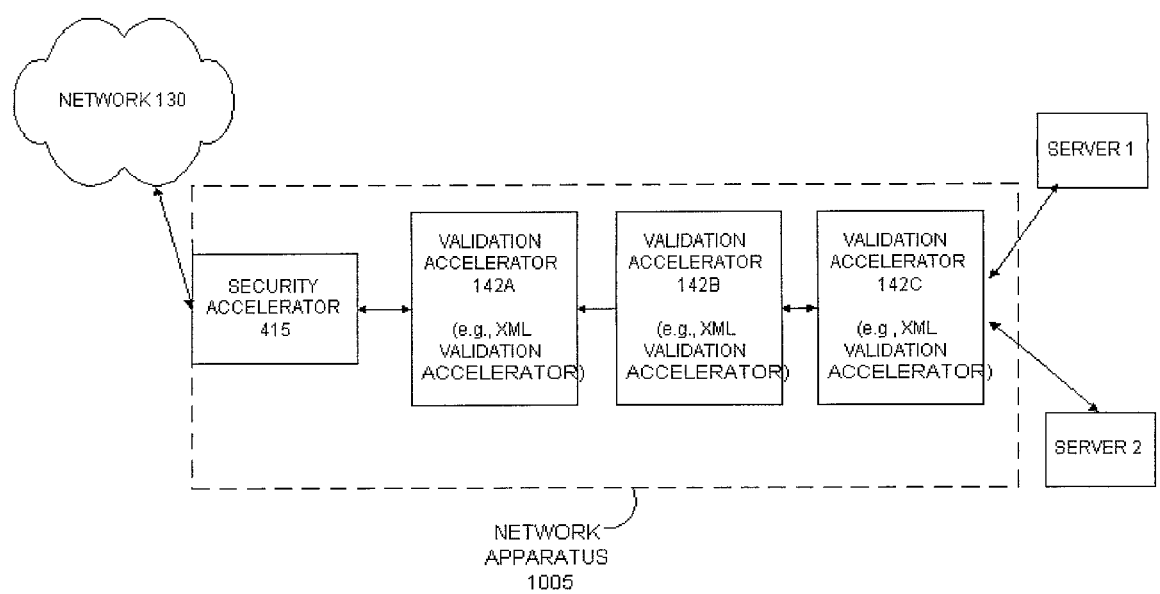
FIG. 10 is a block diagram illustrating an example scalable network apparatus including multiple validation accelerators according to an example embodiment.

In some instances, a single validation accelerator 142 may not be able to handle validation functions for all incoming XML traffic. In such cases, two or more validation accelerators 142 can be cascaded together or (e.g., connected in series) to accommodate increased traffic. FIG. 10 is a block diagram illustrating an example scalable network apparatus including multiple validation accelerators 142 according to an example embodiment. In the example network apparatus 1005 shown in FIG. 10, there are three validation accelerators 142 which are cascaded together (e.g., connected in series): validation accelerators 142A, 142B and 142C. Validation accelerator 142A is coupled to the output of the security accelerator 415. Validation accelerator 142B is coupled to the output of validation accelerator 142A. And, validation accelerator 142C is coupled to the output of validation accelerator 142B. While three validation accelerators are shown in FIG. 10, any number can be cascaded together to provide a validation accelerator having increased capacity (or improved ability to accommodate higher traffic loads).

Figure 11:
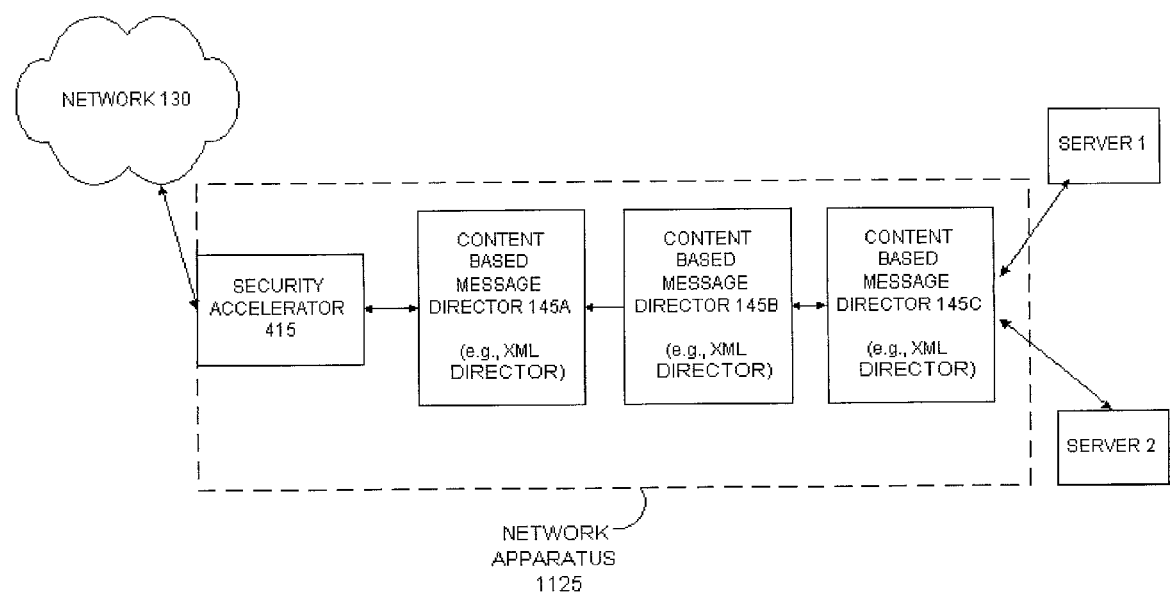
FIG. 11 is a block diagram illustrating an example scalable network apparatus including multiple content based message directors according to an example embodiment.

Likewise, in some cases a single content based message director 145 may not be able to handle the parsing and switching (or directing) of all incoming messages (e.g., of all incoming XML messages). In such cases, two or more content based message directors 145 can be cascaded together (or connected in series together) to handle increased traffic. FIG. 11 is a block diagram illustrating an example scalable network apparatus including multiple content based message directors according to an example embodiment. As shown in FIG. 11, a network apparatus 1125 includes several content based message directors 145 which are cascaded together, including message directors 145A, 145B and 145C. Similar to validation accelerators 142A-C of FIG. 10, the three content based message directors 145A-C of FIG. 11 are cascaded or connected in series between a security accelerator 415 and application servers 1 and 2. While only three message directors 145 are shown in FIG. 11, any number of content based message directors 145 can be cascaded together.

The operation of the network apparatus 1005 (FIG. 10) and network apparatus 1125 (FIG. 11) will now be briefly describe. Note that the following description applies generally to both the validation accelerators 142 of FIG. 10 and the content based message directors 145 of FIG. 11, except where some specific differences are noted. The accelerator 142 and the director 145 will both be generally referred to as a network unit.

Each network unit (e.g., each validation accelerator 142 or message director 145) includes a spillover feature that can be enabled. When the spillover feature is enabled, the network unit determines whether it can process an incoming message based on some loading criteria. If it can process the message, the message is parsed and then processed (i.e., pre-validated for accelerator 142 and directed or routed for director 145). If it cannot process the incoming message based on the criteria, then the message is passed to the next network unit (accelerator 142 or director 145) in series, typically without parsing or processing the application data.

There are many different ways in which a loading criteria can be measured. For example, the accelerator 142 or message director 145 may determine if it can process the incoming message within a predetermined time limit, or determine whether sufficient resources (e.g., processing capacity, memory) are presently available at the network unit to process the message, or determine whether the traffic load (or the processed traffic load) at the network unit has exceeded a threshold. In one simple embodiment, the network unit determines whether it is "busy" or whether it can process the received message. If it is "busy," the message is simply passed (unprocessed) to the next network unit. If the unit can process the message (i.e., not "busy"), then the network unit processes the received message.

The traffic load can be dynamically measured, for example, on a per-connection basis or on a per-packet or per-message basis, and then used to determine which messages should be parsed and processed (i.e., either pre-validated or directed), and which messages should simply be passed to the next network unit (or passed to the application server if the unit is last in series). For example, if the number of connection requests or number of active connections with the network unit exceeds a threshold, then all further received messages (which are associated with other connections) will be passed onto the next network unit, until the number of connections decreases to less than or equal to the threshold. Alternatively, if the traffic load is measured on a per-packet or a per-message basis, then when the number of messages being processed or waiting to be processed at a network unit exceeds a threshold, then all further messages will be passed to the next network unit, until the number of messages being processed or waiting to be processed decreases back to the threshold or less than the threshold. According to yet another embodiment, received messages are placed in a queue at a network unit to await processing at the network unit. The messages are removed from the queue after being processed (e.g., either validated or routed). When the queue at the network unit reaches a predetermined level of fullness, the subsequent messages are then passed onto the next network unit until the queue decreases below the predetermined level of fullness.

A more sophisticated load balancing type algorithm (such as round-robin) can be employed at one or more network units. For example, if there are two network units cascaded together in a network apparatus, the first network unit can automatically pass every other message (or messages associated with every other connection) onto the second network unit in attempt to share the traffic load more evenly across the available cascaded network units.

According to an example embodiment, the security accelerator 415 listens or detects messages (e.g., packets) on a specific port number (e.g., port number 443) where encrypted messages will be received. After being decrypted, the message is then output (decrypted or "in the clear") on a different port number (such as port number 80, which indicates HTTP messages for example). Several security accelerators can also be cascaded together, which cases, the security accelerator can also pass on an encrypted message to the same destination port number (port number 443) because the message is still encrypted. This will cause the message to be decrypted by the next security accelerator 415. The decrypted is finally output by the cascaded group of security accelerators on to the next group of network units (e.g., either message directors 145 or validation accelerators 142).

The processing that goes on at each network unit (either validation accelerator 142 or message director 145) will be briefly described. For the content based message director 145, the processing may include the following (for example):

Determine if the message can be processed (based on the criteria); if it can be processed, then process as follows:
parse the application data
validate the message (or at least a portion of the application data)
either remove the validation instructions and/or add a validation indication (e.g., <?validated by intel?>); a validation indication can be provided in the application data, within a header or specific field of the message or other location
subsequent network units receive the message, detect the validation indication (e.g., in a specific field), and then pass the message on without processing it.

For the validation accelerator 142, the processing may include the following (for example):

Determine if the message can be processed (based on the criteria); if it can be processed, then process as follows:
parse the application data
compare the pattern/query to the application data (e.g., XML data)
if a match is found, then translate the source and/or destination addresses and port numbers, and then output the message.

According to an embodiment, the translated destination address and port number in the message will not match the source address and port number of any subsequent network units in series, and thus, the message will simply be forwarded or passed on; alternatively, after processing, a value can be added to a header in the message or packet or a value added to the application data (or other location in the message) to indicate that the message has been pre-processed, and thus should not be processed again at another network unit.

The network unit (or XML box) can be for either XML Directing or Validation acceleration. They can both use an XML parser.

When the XML box's s spillover option is enabled, if a given XML box (or network unit) cannot process a request within a specified interval, the request is passed on, not parsed, to the next XML box (or network unit) in line.

The last XML box (network unit) on the server side can also be enabled to spill to the server. Spillover is performed dynamically on a connection-by-connection basis (or by packets)

A clear advantage is the ability to scale existing XML directors and or XML validation accelerators and to allow for fail-over if one of the devices stops working.

Another Example Logic Flow

The device will look at all incoming packets (not just connections.)

If the IP address and port number in packet headers is indicated in a mapping then assemble the application data from one or more packets. Hold onto the packet(s) for further processing.
{
  Execute the XML parser.
  If using XML director and a match is found (matches a pattern/query), then convert the matching IP and port pair to the destination IP and port pair and send the converted packets to the next network processing node (next network unit).
  If using XML validation accelerator 142, just validate and then modify the application data (remove validation instructions and/or add validation indication to data) and send the converted packets to the next network processing node/network unit.}

Several embodiments of the present invention are specifically illustrated and/or described herein. However, it will be appreciated that modifications and variations of the present invention are covered by the above teachings and within the purview of the appended claims without departing from the spirit and intended scope of the invention.

What is claimed is:

1. A network apparatus comprising:
   at least one security accelerator to perform encryption or decryption functions on messages;
   a plurality of content based message directors cascaded together, at least one of the content based message directors coupled to the security accelerator, each content based message director to include a spillover feature that can be enabled to spill received messages over from one content based message director to another content based message director, the spillover feature to determine for each content based message director whether the content based message director can process the message based on a loading criteria, each content based message director to route or direct received messages to one of a plurality of application servers based upon XML application data in the message.

2. The network apparatus of claim 1, the loading criteria further comprising at least one of:
   whether the content based message director can process the incoming message within a predetermined time;
   whether the content based message director has sufficient resources to process the message; or
   whether a traffic load at the content based message director exceeds a threshold.

3. A network apparatus comprising:
   at least one security accelerator to perform encryption or decryption functions on messages;
   a plurality of validation accelerators cascaded together, at least one of the validation accelerators coupled to the security accelerator, each validation accelerator to include a spillover feature that can be enabled to spill received messages over from one content based message director to another content based message director, the spillover feature to determine for each validation accelerator whether the validation accelerator can process the message based on a loading criteria, each validation accelerator to validate at least a portion of a message and remove validation instructions from the message and/or add a pre-validation indication to the message before outputting the message.

4. The network apparatus of claim 3, the loading criteria further comprising at least one of:
   whether the validation accelerator can process the incoming message within a predetermined time;
   whether the validation accelerator has sufficient resources to process the message; or
   whether a traffic load at the validation accelerator exceeds a threshold.

5. An apparatus comprising a plurality of validation accelerators cascaded together to validate documents, each validation accelerator to include a spillover feature that can be enabled to spill received messages over from one content based message director to another content based message director, the spillover feature to determine for each validation accelerator whether the validation accelerator can process the message based on a loading criteria, each validation accelerator to receive a message and determine whether the message should be validated, each validation accelerator to validate at least a portion of the received message and to provide an indication in the message that the message has been validated if the validation accelerator determines that the message should be validated, otherwise the validation accelerator to forward the message on to a next validation accelerator or other device without further processing.

6. The apparatus of claim 5 wherein the validation accelerators comprise XML validation accelerators for validating XML documents.

7. The apparatus of claim 5, the loading criteria further comprising at least one of:
   whether the validation accelerator can process the incoming message within a predetermined time;
   whether the validation accelerator has sufficient resources to process the message; or
   whether a traffic load at the validation accelerator exceeds a threshold.

* * * * *

UNITED STATES PATENT AND TRADEMARK OFFICE
CERTIFICATE OF CORRECTION

| | | |
|---|---|---|
| PATENT NO. | : 7,512,711 B1 | Page 1 of 1 |
| APPLICATION NO. | : 09/566800 | |
| DATED | : March 31, 2009 | |
| INVENTOR(S) | : John B. Abjanic, David A. Marlatt and John A. Malo | |

It is certified that error appears in the above-identified patent and that said Letters Patent is hereby corrected as shown below:

On the title page, item 63, in the "Related U.S. Application Data", change "09/566,800" to --09/562,104--

In the Specification

Column 1, lines 13 to 14, change "09/566,800" to --09/562,104--

Signed and Sealed this
Eighth Day of September, 2015

Michelle K. Lee
*Director of the United States Patent and Trademark Office*